(12) United States Patent
Horning et al.

(10) Patent No.: US 10,598,646 B1
(45) Date of Patent: Mar. 24, 2020

(54) HIGH DEW POINT HUMIDITY SENSOR

(71) Applicant: Reading Terminal Systems, Inc., Sinking Spring, PA (US)

(72) Inventors: David C. Horning, Lebanon, PA (US); Richard J. Starke, Temple, PA (US)

(73) Assignee: Reading Thermal Systems, Inc., Sinking Spring, PA (US)

( * ) Notice: Subject to any disclaimer, the term of this patent is extended or adjusted under 35 U.S.C. 154(b) by 0 days.

(21) Appl. No.: 16/439,075

(22) Filed: Jun. 12, 2019

Related U.S. Application Data

(60) Provisional application No. 62/779,107, filed on Dec. 13, 2018.

(51) Int. Cl.
*G01N 33/00* (2006.01)
*A21B 3/04* (2006.01)

(52) U.S. Cl.
CPC .......... *G01N 33/0016* (2013.01); *A21B 3/04* (2013.01); *G01N 33/0036* (2013.01)

(58) Field of Classification Search
CPC ... G01N 33/0016; G01N 33/0036; A21B 3/04
USPC ........................................................ 73/23.21
See application file for complete search history.

(56) References Cited

U.S. PATENT DOCUMENTS

| | | | | |
|---|---|---|---|---|
| 2013/0168548 A1* | 7/2013 | Wang | ................... | G01N 33/497 250/288 |
| 2013/0265064 A1* | 10/2013 | Hamann | ................ | G01N 17/04 324/700 |

OTHER PUBLICATIONS

Vaisala DRYCAP Sensor for Measuring Dew Point, Vaisala, 2012, downloaded from web page: https://www.vaisala.com/sites/default/files/documents/DRYCAP-Technology-description-B210981EN-B.pdf, Download date: Nov. 12, 2019, 2 pages.

DMT345 and DMT346 Dewpoint Transmitters for Hight Temperature Applications, Vaisala, 2017, downloaded from web page: https://www.vaisala.com/sites/default/files/documents/DMT345-DMT346-Datasheet-B210723EN.pdf, Download date: Nov. 12, 2019, 5 pages.

Dew Point Transmitters DMT345 and DMT346 for High Temperature Applications, Vaisala, downloaded from web page: https://www.vaisala.com/en/products/instruments-sensors-and-other-measurement-devices/instruments-industrial-measurements/dmt345-346, Download date: Nov. 12, 2019, original posting date: unknown, 3 pages.

* cited by examiner

*Primary Examiner* — Tarun Sinha
(74) *Attorney, Agent, or Firm* — Panitch Schwarze Belisario & Nadel LLP

(57) ABSTRACT

A high dew point humidity sensor includes an enclosure assembly, an ambient temperature sensor, air sample intake and exhaust openings, a fluid-moving device, a heater block assembly, an internal temperature sensor, a humidity sensor chip, and a controller. The controller is configured to: (i) collect a measured ambient temperature from the ambient temperature sensor; (ii) collect a measured humidity of sample air from the humidity sensor chip; (iii) collect a measured temperature from the internal temperature sensor; and (iv) control operation of the heater block assembly based, at least in part, on the measured ambient temperature and the measured temperature from the internal temperature sensor.

17 Claims, 6 Drawing Sheets

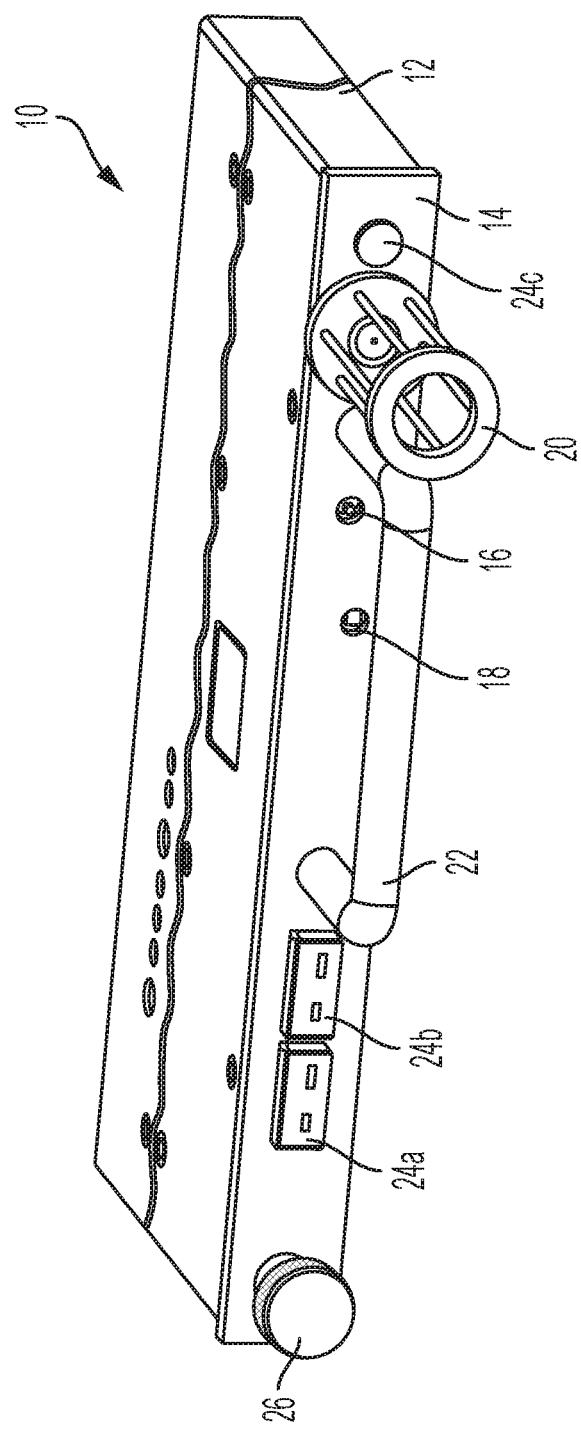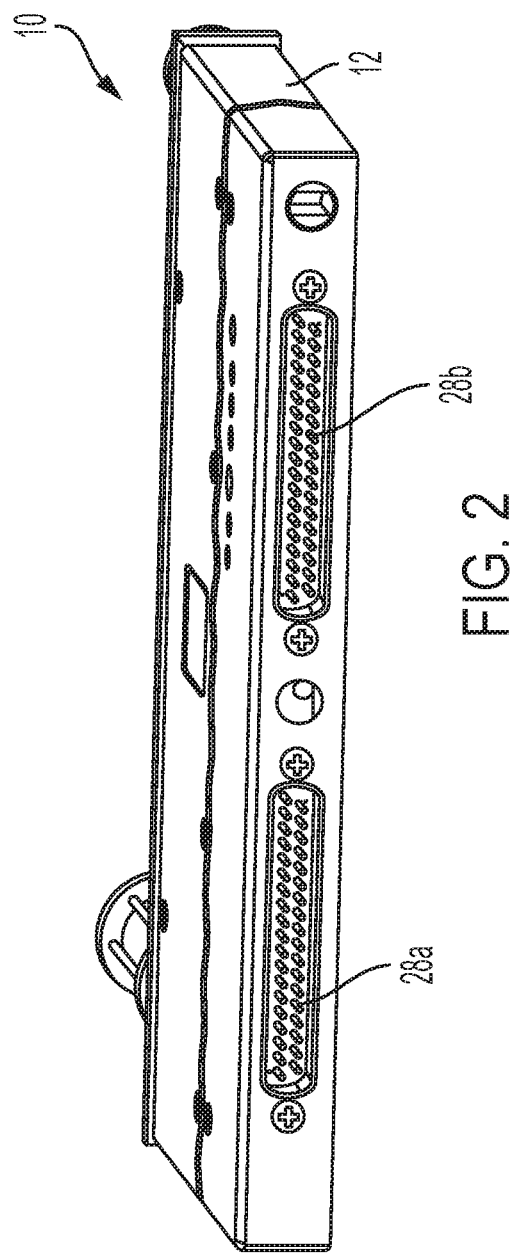

HIGH DEW POINT HUMIDITY SENSOR

CROSS-REFERENCE TO RELATED APPLICATIONS

This application claims the benefit of U.S. Provisional Patent Application No. 62/779,107, filed on Dec. 13, 2018, entitled "High Dew Point Humidity Sensor," the entire contents of which are incorporated by reference herein.

BACKGROUND OF THE INVENTION

Embodiments of the present invention relate generally to a humidity sensor for high dew point processes, and more particularly, to a humidity sensor that reduces or prevents condensation from accumulating on the sensor or relevant components associated therewith.

Measuring relative humidity during high dew point processes, such as may be encountered within ovens, proofers, dryers, cooling tunnels, or the like, can be a difficult but necessary operation. For example, it can be important in commercial baking operations to monitor various baking parameters within the oven, such as temperature, air flow, heat flux, and humidity. Inconsistencies or undesirable changes in any of these parameters can result in poor quality product returning from the oven. To that end, there is equipment, for example the SCORPION® line of data sensors and loggers available from Applicant, which can be passed through a commercial baking oven with product under full load and at full temperatures, to track the above-mentioned parameters. The various sensors are generally housed in a thermal barrier or insulator block to protect sensitive electronics.

Humidity sensors constitute one type of this equipment. However, many humidity sensor chips are not rated for the extreme temperatures found in commercial ovens (e.g., 500° F. or more). Thus, the humidity sensor chips are often contained within a housing having a sample air channel formed therein, which cools the air before passing it over the humidity sensor chip. This protects the humidity sensor chip from the extreme oven temperatures, but it also becomes difficult to keep the humidity sensor chip at a temperature above the dew point found in the oven. As a result, condensation is likely to form and block the sample air channel or contact the humidity sensor chip.

One method used to address condensation involves using a heating pad to pre-heat the humidity sensor to, for example, 100-110° F. Once these temperatures are reached, the humidity sensor can be inserted into the thermal barrier and run through the oven to do a test profile. If results are good from the trial run, an actual run for humidity sensing can be performed. If there is condensation however, the data will be poor, and the humidity sensor must be heated further before doing another test. This is a labor-intensive process involving much trial-and-error, which also makes it near impossible to use a humidity sensor in commercial ovens having multiple zones with different temperatures and/or other baking parameters.

It is therefore desirable to provide a high dew point humidity sensor that can avoid developing harmful condensation during use without employing unrefined trial-and-error preheating techniques, and which can also be utilized in multi-zone high temperature equipment.

BRIEF SUMMARY OF THE INVENTION

Briefly stated, an embodiment of the present invention comprises a high dew point humidity sensor that includes an enclosure assembly and an ambient temperature sensor connected to the enclosure assembly and configured to measure an ambient temperature of air external to the enclosure assembly. An air sample intake opening and an air sample exhaust opening are formed in the enclosure assembly and are in fluid communication with each other. A fluid-moving device is located within the enclosure assembly. The fluid-moving device is in fluid communication with the air sample intake opening via an air sample intake tube and in fluid communication with the air sample exhaust opening. A heater block assembly is located within the enclosure assembly and is in thermal communication with at least a portion of the air sample intake tube. An internal temperature sensor is located within the enclosure assembly and is positioned to be in thermal communication with the air sample intake tube. A humidity sensor chip is located within the enclosure assembly and is positioned to be in fluid communication with at least a portion of sample air flowing within the air sample intake tube during operation. The humidity sensor chip is configured to measure humidity of the sample air. A controller is located within the enclosure assembly and is configured to: (i) collect the measured ambient temperature from the ambient temperature sensor; (ii) collect the measured humidity of the sample air from the humidity sensor chip; (iii) collect a measured temperature from the internal temperature sensor; and (iv) control operation of the heater block assembly based, at least in part, on the measured ambient temperature and the measured temperature from the internal temperature sensor.

Another embodiment of the present invention comprises a method for controlling operation of a heater block assembly in thermal communication with an air sample intake tube within an enclosure assembly of a high dew point humidity sensor. The method includes receiving, by a controller of the high dew point humidity sensor, a measured ambient temperature of air external to the enclosure assembly, receiving, by the controller from a humidity sensor chip in fluid communication with at least a portion of sample air flowing within the air sample intake tube, a measured humidity of the sample air, receiving, by the controller from an internal temperature sensor in thermal communication with the air sample intake tube, a measured temperature, updating, by the controller, a setpoint temperature to be equal to the measured ambient temperature plus a predetermined buffer, calculating, by the controller based at least on the updated setpoint temperature and the measured temperature from the internal temperature sensor, a pulse width modulation (PWM) duty cycle to apply to the heater block assembly, and applying, by the controller, the calculated PWM duty cycle to the heater block assembly.

BRIEF DESCRIPTION OF THE SEVERAL VIEWS OF THE DRAWINGS

The following detailed description of preferred embodiments of the invention will be better understood when read in conjunction with the appended drawings. For the purpose of illustration, there are shown in the drawings embodiments which are presently preferred. It should be understood, however, that the invention is not limited to the precise arrangements and instrumentalities shown.

In the drawings:

FIG. 1 is a front side perspective view of the high dew point humidity sensor in accordance with a preferred embodiment of the present invention;

FIG. 2 is a rear side perspective view of the high dew point humidity sensor of FIG. 1;

DETAILED DESCRIPTION OF THE INVENTION

Figure 3:
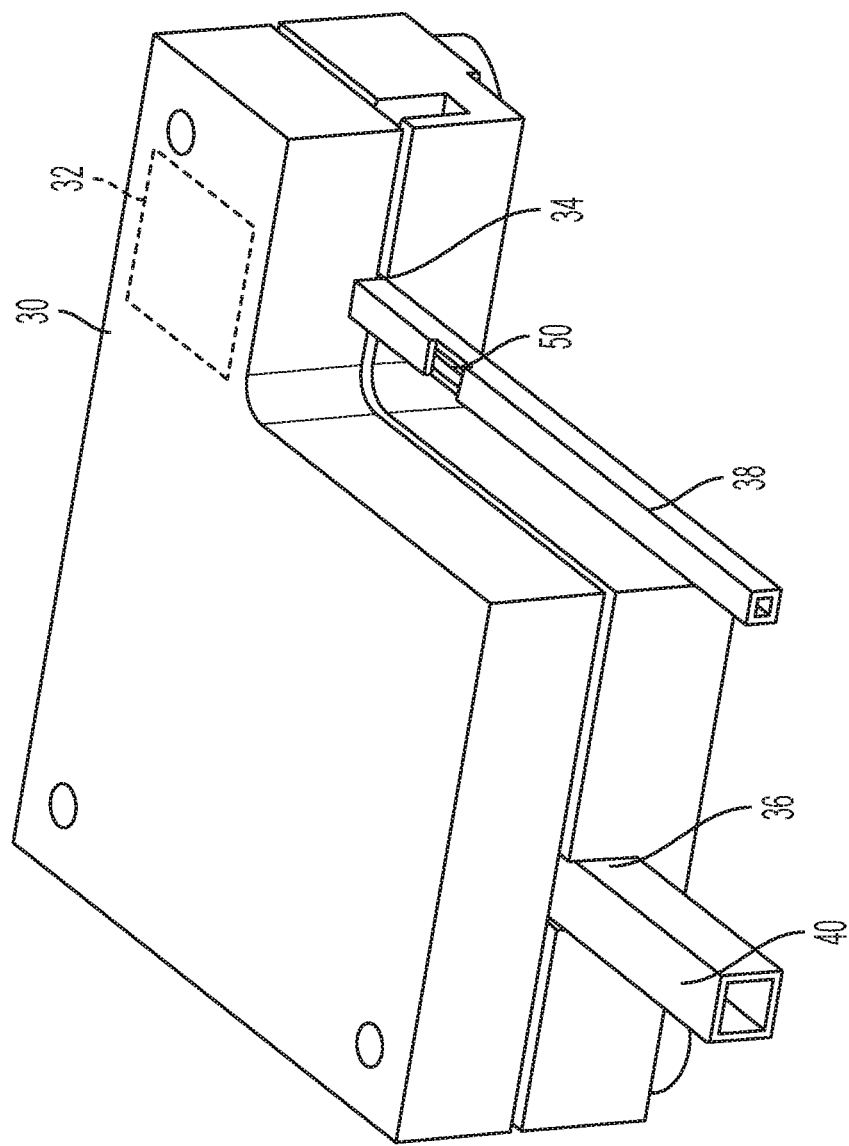
FIG. 3 is a front side perspective view of a fan housing for use in the high dew point humidity sensor of FIG. 1.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the device and designated parts thereof. The terminology includes the above-listed words, derivatives thereof, and words of similar import. Additionally, the words "a" and "an", as used in the claims and in the corresponding portions of the specification, mean "at least one."

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIG. 1, there is shown a high dew point humidity sensor 10 in accordance with a preferred embodiment of the present invention. The high dew point humidity sensor 10 preferably includes an enclosure assembly 12 that is sized and shaped to allow insertion of the high dew point humidity sensor 10 into an insulated thermal barrier (not shown), which is placed in an oven (not shown), for example. Preferably, the thermal barrier receives the enclosure assembly 12 in such a way that only a front panel 14 of the high dew point humidity sensor 10 is exposed to ambient air within the oven. Thus, the enclosure assembly 12 is insulated by the thermal barrier during operation. However, the high dew point humidity sensor 10 may be configured to be used as a standalone device, in which case the enclosure assembly 12 may be designed to include its own insulation.

The front panel 14 preferably includes an air sample intake opening 16 and an air sample exhaust opening 18 formed therethrough, and are in fluid communication with each other. As will be explained in more detail below, air within the oven to be sampled is drawn into the air sample intake opening 16, sampled for humidity readings within the enclosure assembly 12, and then expelled through the air sample exhaust opening 18.

The front panel 14 further preferably includes an ambient temperature sensor 20 configured to measure the temperature of the air within the oven during operation. The ambient temperature sensor 20 may be for example, a thermocouple having a digital converter. This data is later utilized by the high dew point humidity sensor 10 to control operation of heaters 46 (FIG. 4) in thermal communication with sample air brought in through the air sample intake opening 16, as will be explained in further detail below.

The front panel 14 may further include a handle 22 to allow for easy manual removal of the high dew point humidity sensor 10 from the thermal barrier or other assembly which may receive the high dew point humidity sensor 10, such as a carrying case (not shown) or the like. The front panel 14 may further provide one or more sensor inputs 24a, 24b, 24c configured to allow electrical and/or data connections to external sensor devices, such as probes (not shown) or the like. The front panel 14 further preferably includes a control knob 26 to allow the user to power the high dew point humidity sensor 10 on or off and to actuate various operating modes, such as to start recording, or the like. In some embodiments, the control knob 26 may be a shaft that connects to a switch on an adjacent component, such as a data logger (not shown). While a control knob 26 is shown, other conventional user interfaces, such as keys, switches, touchpads, or the like may be used as well, provided they are capable to withstand commercial oven temperatures. It is contemplated that other such control interfaces may be provided on various faces of the enclosure assembly 12, but it is preferred that at least some basic operating interface be provided on the front panel 14 to allow basic operational control (e.g., power on, start recording, or the like) while the high dew point humidity sensor 10 is mounted within the thermal barrier.

Referring to FIG. 2, the high dew point humidity sensor 10 preferably also includes one or more I/O ports 28a, 28b, through which recorded data may be transferred, operational instructions may be received, or the like. For example, the high dew point humidity sensor 10 may use the I/O ports 28a, 28b to connect to a data logger, such as the SCORPION® 2 Data Logger, available from the Applicant. Thus, the I/O ports 28a, 28b are preferably 32-pin D-Sub connectors and utilize I$^2$C serial communication protocol for data transfer, although other connector and protocol types may be used without departing from the spirit and scope of the present invention. In a preferred embodiment, one or more of the sensor inputs 24a, 24b may connect directly to the I/O ports 28a, 28b to provide data directly to the data logger, while other sensor inputs 24c may interface with controller circuitry (e.g., controller U2 (FIG. 6)) within the high dew point humidity sensor 10. The I/O ports 28a, 28b may also provide a connection to supply power to the various components of the high dew point humidity sensor 10. The I/O ports 28a, 28b may be located on a rear side of the enclosure assembly 12, although other locations on the enclosure assembly 12 may be just as suitable.

The high dew point humidity sensor 10 preferably includes a fluid-moving device that is used to draw sample air from the oven into the air sample intake opening 16 of the enclosure assembly 12. The fluid-moving device may be, for example, a fan, a piezoelectric or other type of blower, a pump, or the like. Referring to FIG. 3, the fluid-moving device in the presently described embodiment is a fan 32 provided within a fan housing 30. The fan housing 30 is preferably located within the enclosure assembly 12. The fan 32 may be, for example, a UB393-500 fan blower available from SUNON INC. in Brea, Calif. The fan housing 30 preferably includes an intake opening 34 that leads to an integrally formed intake channel (not shown) within the fan housing 30, through which sample air may be led to the fan 32. Similarly, the fan housing 30 also preferably includes an exhaust opening 36 connected to an integrally formed exhaust channel (not shown) within the fan housing 30. Sample air exits the fan 32 and moves through the exhaust channel to be expelled through the exhaust opening 36.

An air sample intake tube 38 is provided to connect the air sample intake opening 16 of the enclosure assembly 12 to the intake opening 34 in the fan housing 30. As will be explained in further detail below, it is preferred that the air sample intake tube 38 be made from a material having a high thermal conductivity, so that sample air in the air sample intake tube 38 can be heated or cooled as it is drawn toward the fan 32. In one embodiment, for example, the air sample intake tube 38 is made from brass, although other metals or the like may be used as well. An air sample exhaust tube 40 is also provided to connect the exhaust opening 36 in the fan housing 30 to the air sample exhaust opening 18 in the enclosure assembly 12. The air sample exhaust tube 40 may also be made of brass, although other types of materials capable of withstanding oven temperatures may also be used as well. Where the air sample intake and/or exhaust tubes 38, 40 are made of brass, the tubes 38, 40 may further be gold-plated to further prevent corrosion. In some embodiments, the air sample intake tube 38 and air sample exhaust tube 40 may connect directly to the fan 32, rather than via integrally formed channels in the fan housing 30.

Figure 4:
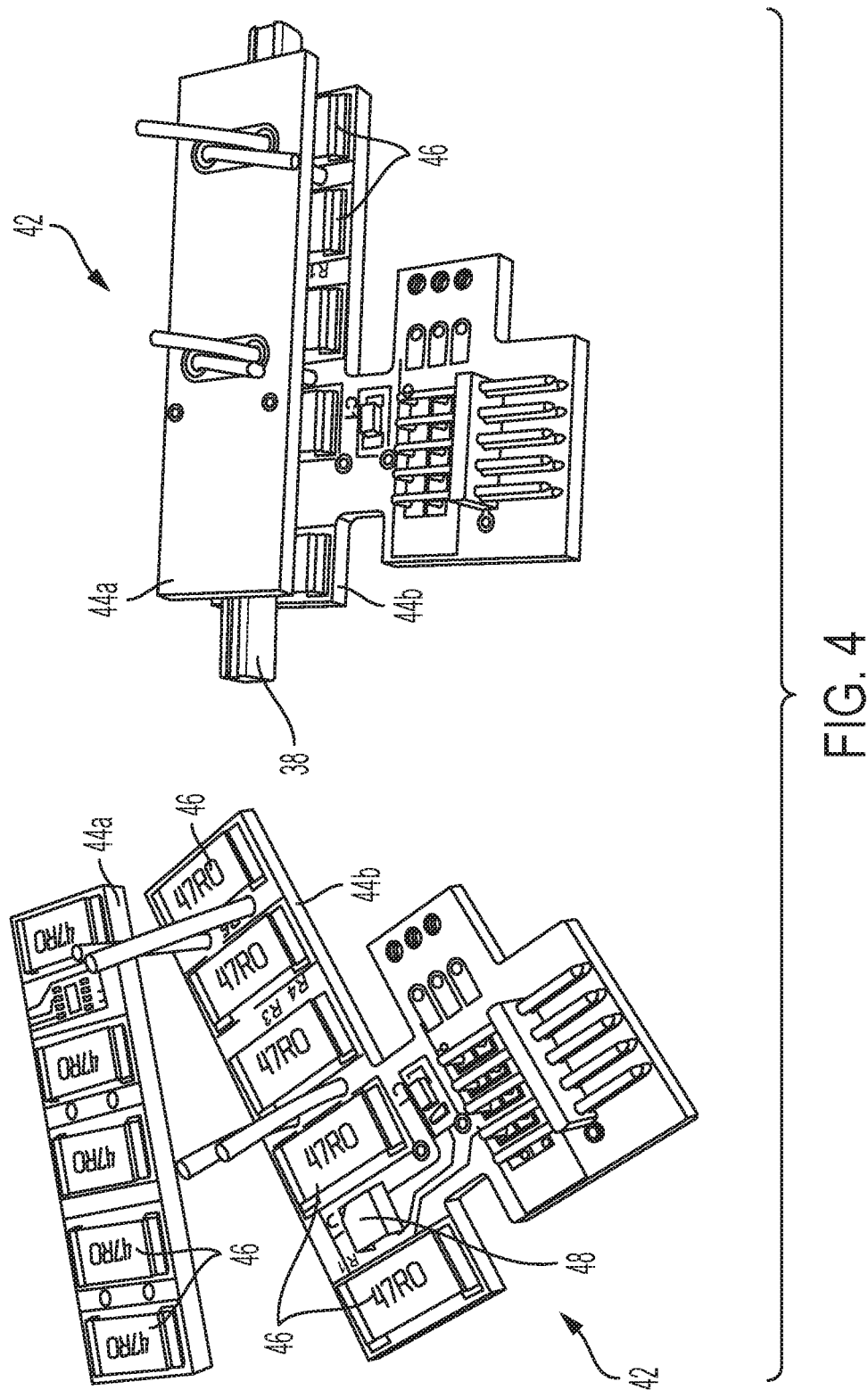
FIG. 4 includes assembled and disassembled views of a heater block assembly for use in the high dew point humidity sensor of FIG. 1.

Referring to FIG. 4, there are shown assembled and disassembled views of a heater block assembly 42 for use with the high dew point humidity sensor 10 in accordance with a preferred embodiment of the present invention. In the embodiment shown in FIG. 4, the heater block assembly 42 is shown as including a pair of heater circuit boards 44a, 44b. Each heater circuit board 44a, 44b preferably includes a plurality of heaters 46 formed thereon or attached thereto. The heaters 46 are preferably resistive heaters, and are pulse width modulation (PWM) controlled in conjunction with the ambient air temperature and an internally measured temperature, as explained more fully below. When assembled, the heater circuit boards 44a, 44b preferably surround the air sample intake tube 38 so as to bring the heaters 46 into thermal contact or thermal communication with the air sample intake tube 38, allowing the sample air travelling within the air sample intake tube 38 to be heated as desired.

An internal temperature sensor is provided and preferably located within the enclosure assembly 12, and is positioned to be in thermal communication with the air sample intake tube 38. In a preferred embodiment, the internal temperature sensor is disposed on a humidity sensor chip 48, which is also capable of measuring humidity of sample air brought into contact therewith. For example, the humidity sensor chip 48 may be included on one of the heater circuit boards 44a, 44b. The humidity sensor chip 48 may be, for example, the SHT35-DIS-F2.5kS humidity and temperature sensor available from SENSIRION AG of Switzerland. When the heater block assembly 42 is assembled, the humidity sensor chip 48 is preferably aligned with a vent 50 (FIG. 3) formed in the air sample intake tube 38, which allows some of the sample air to reach the humidity sensor chip 48 for analysis.

While the humidity sensor chip 48 is shown mounted on one of the heater circuit boards 44b in the embodiment of FIG. 4, the humidity sensor chip 48 may alternatively be mounted to its own, separate circuit board (not shown) or other type of support substrate. In addition, the heaters 46 may alternatively each be provided with their own individual heater circuit boards 44, may be provided on common or individual support substrates, or may be attached directly to the air sample intake tube 38. Heaters 46 may also optionally be used in conjunction with the air sample exhaust tube 40. Moreover, the internal temperature sensor may be provided separately from any humidity sensor or chip.

In some embodiments, a thermal epoxy (not shown) may be added around one or more of the heaters 46, the air sample intake tube 38, the humidity sensor chip 48, and the internal temperature sensor.

Figure 5:
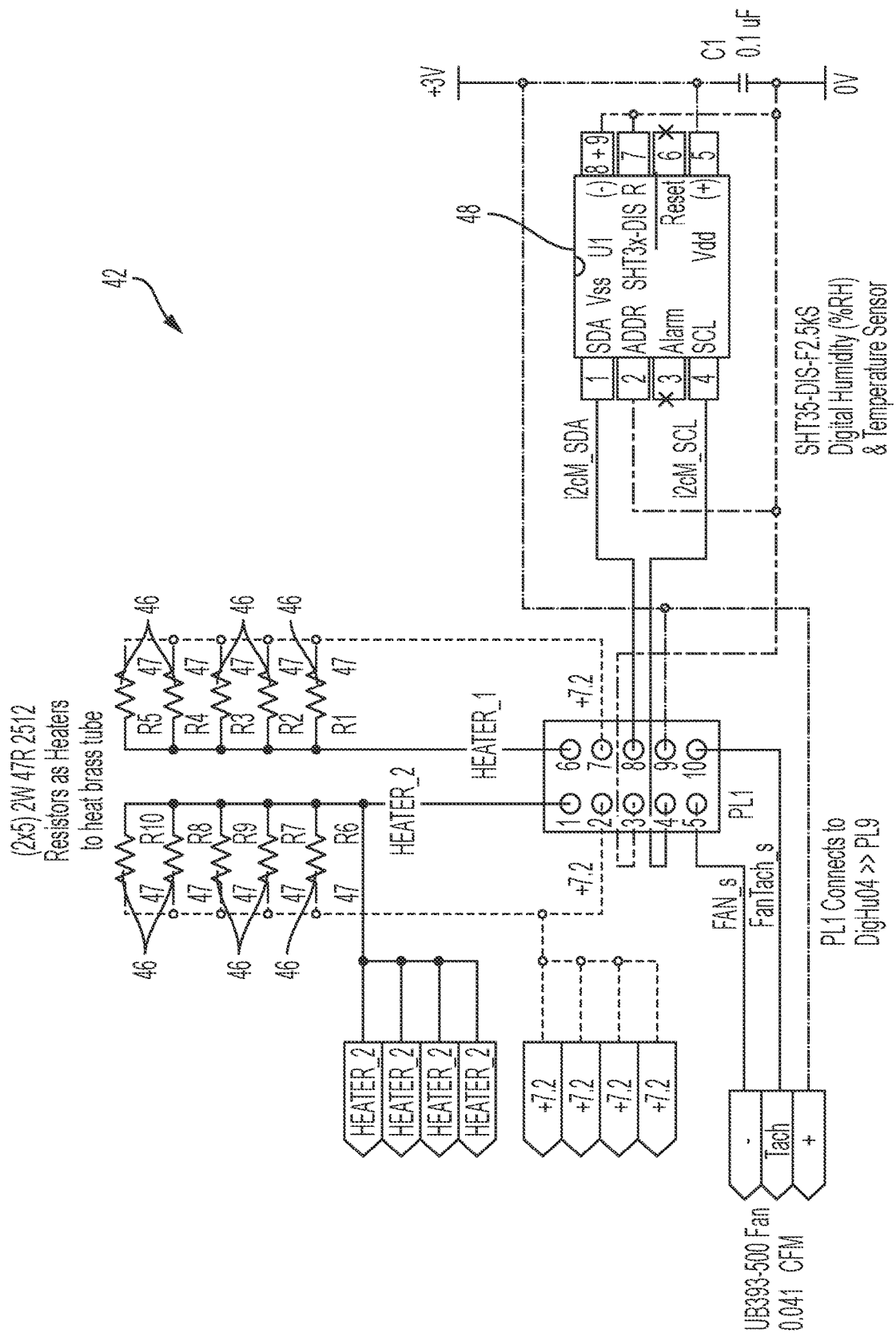
FIG. 5 is a schematic circuit diagram of the heater block assembly of FIG. 4.

FIG. 5 is a circuit schematic of the heater block assembly 42, which includes the humidity sensor chip 48 and the heaters 46. A connection may also be provided on the heater block assembly 42 for the fan 32, although the fan 32 can be controlled separately from the heater block assembly 42.

Figure 6:
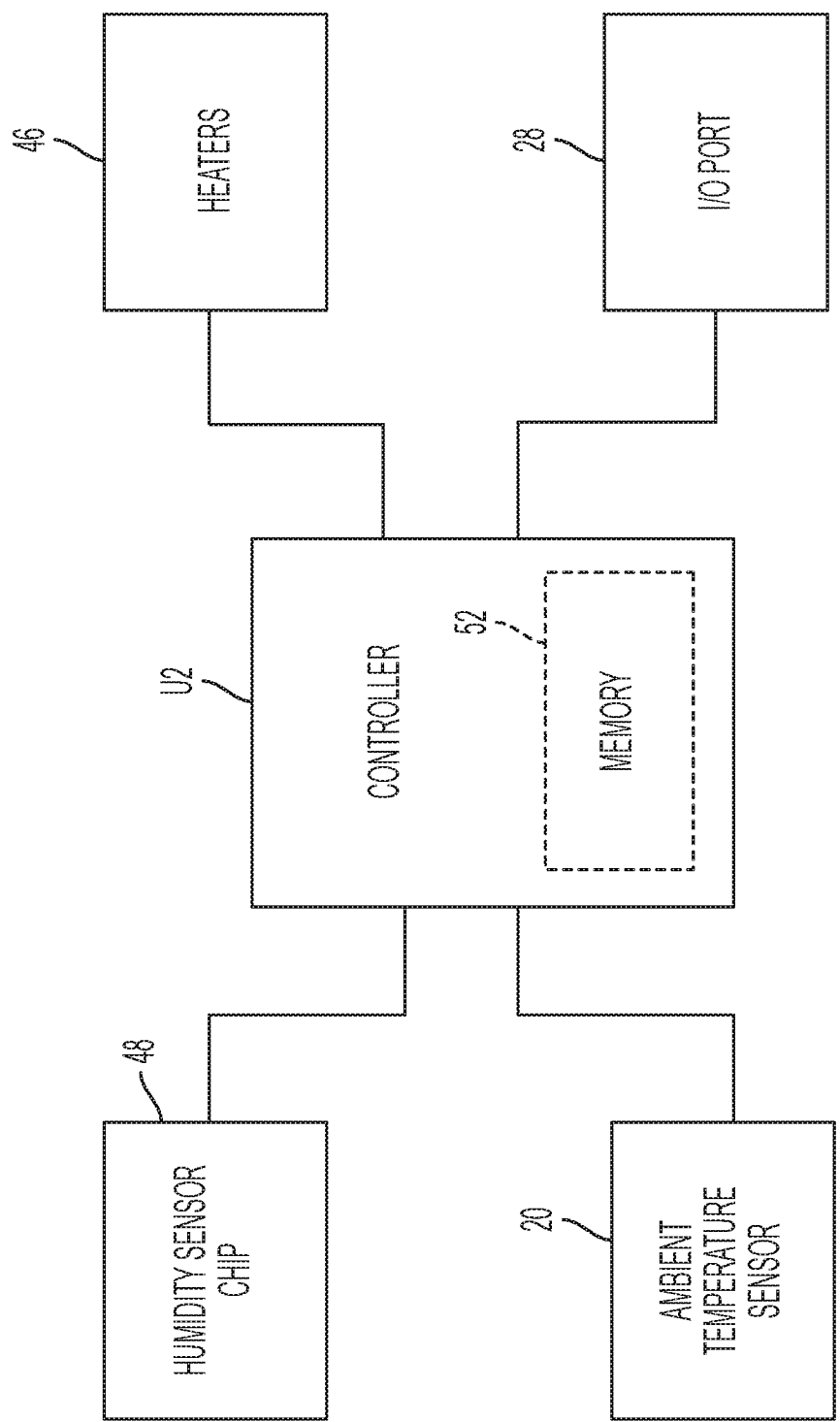
FIG. 6 is a schematic block diagram of various components of the high dew point humidity sensor of FIG. 1.

FIG. 6 is a schematic block diagram of various components of the high dew point humidity sensor 10 according to one embodiment. A controller U2 is preferably provided for controlling operation of the high dew point humidity sensor 10. The controller U2 may be any type of controller, such as a microprocessor, multiple processors, or the like. The controller U2 preferably includes or is operatively coupled to a memory 52 that may store code or software for carrying out the processes described below, or for carrying out other operations of the high dew point humidity sensor 10, and may store any captured data for later transfer to external devices. The memory 52 is preferably a flash memory integrated into the controller U2, but can also be any known or suitable memory device such as random access memory (RAM), read only memory (ROM), flash RAM, hard disk, or the like. The controller U2 is preferably in communication with the humidity sensor chip 48 (which, in this embodiment, includes the internal temperature sensor) and the ambient temperature sensor 20 and is configured to collect data from each during sampling of the oven air. Based on temperature readings from both the internal temperature sensor of the humidity sensor chip 48 and the ambient temperature sensor 20, the controller U2 adjusts a PWM signal to the heaters 46. Moreover, collected data, such as humidity data, can be sent by the controller U2 to the I/O port(s) 28 for communication to the data logger.

Figure 7:
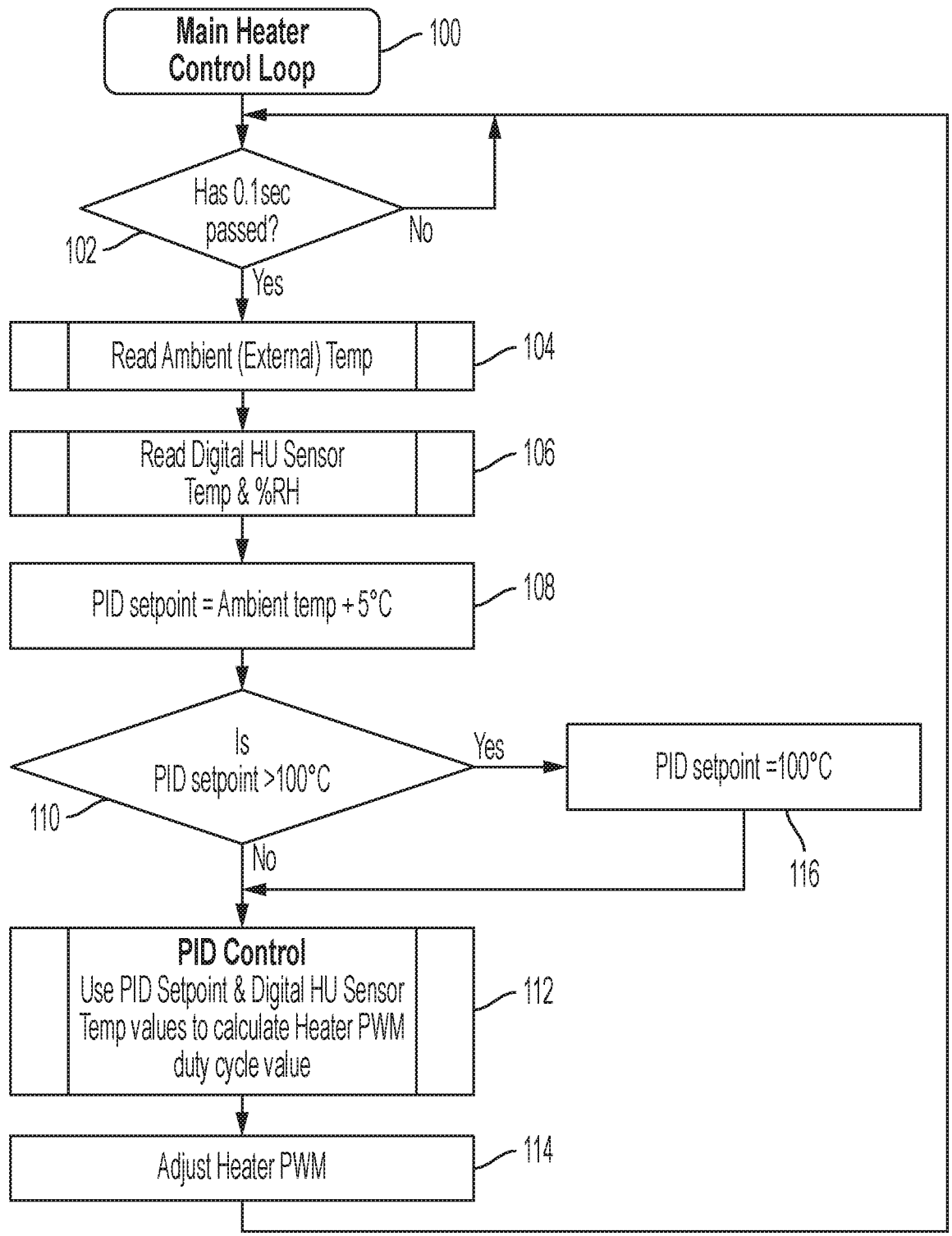
FIG. 7 is a flow diagram illustrating a method of operating the heaters of FIG. 4 during use of the high dew point humidity sensor of FIG. 1.

Operation of the heaters 46 in the high dew point humidity sensor 10 will now be described with respect to FIG. 7. The heaters 46 are preferably operated using a PID main control loop 100. At step 102, the controller (preferably controller U2, although other controllers, such as a dedicated heater controller, for example, may be used instead) checks whether a preset time period has passed. In the example of FIG. 7, the PID loop 100 updates every tenth (0.1) of a second, although the time period may be adjusted up or down as desired for the specific application. At step 104, the controller U2 retrieves the ambient temperature of the oven as read by the ambient temperature sensor 20. At step 106, the controller U2 reads the relative humidity of the sample air from the humidity sensor chip 48, and collects a measured temperature from the internal temperature sensor. It should be noted that steps 104 and 106 can also be performed in reverse order or substantially simultaneously with one another.

At step 108, the PID setpoint is updated to equal the measured ambient temperature plus a predetermined buffer. In the embodiment shown in FIG. 7, the PID setpoint is equal to the measured ambient temperature raised by about 5° C. It has been found that if, as the oven heats up, the air sample intake tube 38 can be maintained at about 5° C. above the oven temperature, build-up of condensation on or within the high dew point humidity sensor 10 can be reduced or prevented. However, this condition is generally no longer necessary once the temperature of the air sample intake tube 38 exceeds 100° C. (i.e., the boiling point of water). Thus, at step 110, the controller U2 determines whether the adjusted PID setpoint exceeds a predetermined threshold temperature, in this case, 100° C. If not, at step 112, the controller uses the PID setpoint and the measured temperature from the internal temperature sensor on the humidity sensor chip 48 to calculate a PWM duty cycle value applied to the heaters 46. At step 114, the PWM to the heaters 46 is adjusted, and the loop returns to step 102. In one preferred embodiment, PWM adjustments are proportional to the relative difference in temperature between the PID setpoint and sample air temperature measured by the internal temperature sensor on the humidity sensor chip 48. For example, the PWM will increase by a greater amount the farther the sample air temperature is below the PID setpoint. Similarly, the PWM will decrease by a greater amount the farther the sample air temperature is above the PID setpoint.

If, on the other hand, the controller U2 determines that the PID setpoint exceeds the predetermined threshold temperature, at step 116, the controller U2 resets the PID setpoint to the predetermined threshold temperature. For the embodiment of FIG. 7, the PID setpoint is set to be 100° C. whenever the PID setpoint calculated at step 108 exceeds about 100° C. Once the PID setpoint is reset, the controller U2 moves to step 112, as explained earlier.

Those skilled in the art will recognize that boundaries between the above-described operations are merely illustrative. The multiple operations may be combined into a single operation, a single operation may be distributed in additional operations and operations may be executed at least partially overlapping in time. Further, alternative embodiments may include multiple instances of a particular operation, and the order of operations may be altered in various other embodiments.

While the high dew point humidity sensor 10 has been described herein as being utilized for humidity measurements in a commercial oven, the sensor may also be used in conjunction with other equipment capable of generating high dew points, such as proofers, dryers, cooling tunnels, or the like, or in applications where the dew point may exceed the starting temperature of the sensor.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A high dew point humidity sensor comprising:
an enclosure assembly;
an ambient temperature sensor connected to the enclosure assembly and configured to measure an ambient temperature of air external to the enclosure assembly;
an air sample intake opening and an air sample exhaust opening formed in the enclosure assembly and in fluid communication with each other;
an air sample intake tube located within the enclosure assembly and in fluid communication with the air sample intake opening;
a fluid-moving device located within the enclosure assembly, the fluid-moving device being in fluid communication with the air sample intake opening via the air sample intake tube and in fluid communication with the air sample exhaust opening;
a heater block assembly located within the enclosure assembly and in thermal communication with at least a portion of the air sample intake tube to enable heating of the air sample intake tube by the heater block assembly;
an internal temperature sensor located within the enclosure assembly and positioned to be in thermal communication with the air sample intake tube;
a humidity sensor chip located within the enclosure assembly and positioned to be in fluid communication with at least a portion of sample air flowing within the air sample intake tube during operation, the humidity sensor chip being configured to measure humidity of the sample air; and
a controller located within the enclosure assembly and configured to:
(i) collect the measured ambient temperature from the ambient temperature sensor,
(ii) collect the measured humidity of the sample air from the humidity sensor chip,
(iii) collect a measured temperature from the internal temperature sensor, and
(iv) control operation of the heater block assembly based, at least in part, on the measured ambient temperature and the measured temperature from the internal temperature sensor.

2. The high dew point humidity sensor of claim 1, wherein the heater block assembly includes a pair of heater circuit boards, each of the heater circuit boards including a plurality of resistive heaters in thermal communication with at least a portion of the air sample intake tube.

3. The high dew point humidity sensor of claim 2, wherein the controller is configured to control operation of the heater block assembly by adjusting a pulse width modulation (PWM) signal to the resistive heaters based, at least in part, on the measured ambient temperature and the measured temperature from the internal temperature sensor.

4. The high dew point humidity sensor of claim 2, wherein the humidity sensor chip is located on one of the heater circuit boards.

5. The high dew point humidity sensor of claim 1, wherein the enclosure assembly includes a front panel configured for exposure to the external air, the front panel including the ambient temperature sensor, the air sample intake opening, and the air sample exhaust opening.

6. The high dew point humidity sensor of claim 5, wherein the enclosure assembly is sized and shaped for insertion into a thermal barrier such that, upon insertion into the thermal barrier, only the front panel of the enclosure assembly is exposed to the external air.

7. The high dew point humidity sensor of claim 1, further comprising at least one I/O port configured for connection to a device external to the enclosure assembly and in communication with the controller, the controller being further configured to send at least the measured humidity of the sample air to the at least one I/O port.

8. The high dew point humidity sensor of claim 1, wherein the air sample intake tube includes a vent, the humidity sensor chip being aligned with the vent.

9. The high dew point humidity sensor of claim 1, wherein the air sample intake tube is made of brass.

10. The high dew point humidity sensor of claim 1, wherein the internal temperature sensor is disposed on the humidity sensor chip.

11. The high dew point humidity sensor of claim 1, wherein the controller is configured to control operation of the heater block assembly by adjusting a pulse width modulation (PWM) signal to the heater block assembly based, at least in part, on the measured ambient temperature and the measured temperature from the internal temperature sensor.

12. A method for controlling operation of a heater block assembly in thermal communication with an air sample intake tube within an enclosure assembly of a high dew point humidity sensor, the method comprising:
receiving, by a controller of the high dew point humidity sensor, a measured ambient temperature of air external to the enclosure assembly;
receiving, by the controller from a humidity sensor chip in fluid communication with at least a portion of sample air flowing within the air sample intake tube, a measured humidity of the sample air;
receiving, by the controller from an internal temperature sensor in thermal communication with the air sample intake tube, a measured temperature;
updating, by the controller, a setpoint temperature to be equal to the measured ambient temperature plus a predetermined buffer;
calculating, by the controller based at least on the updated setpoint temperature and the measured temperature from the internal temperature sensor, a pulse width modulation (PWM) duty cycle to apply to the heater block assembly; and
applying, by the controller, the calculated PWM duty cycle to the heater block assembly.

13. The method of claim 12, further comprising:
after updating the setpoint temperature, determining, by the controller, whether the updated setpoint temperature exceeds a threshold temperature; and
when the updated setpoint temperature exceeds the threshold temperature, changing, by the controller, the setpoint temperature to be equal to the threshold temperature.

14. The method of claim 13, wherein the threshold temperature is about 100° C.

15. The method of claim 12, wherein the predetermined buffer is about 5° C.

16. The method of claim 12, wherein calculating the PWM duty cycle is based at least on a relative difference between the updated setpoint temperature and the measured temperature from the internal temperature sensor.

17. The method of claim 12, wherein the internal temperature sensor is disposed on the humidity sensor chip.

* * * * *